United States Patent [19]

Kelly et al.

[11] Patent Number: 5,650,534

[45] Date of Patent: Jul. 22, 1997

[54] OPTICALLY ACTIVE SMECTIC PHOTO-CROSS-LINKABLE LIQUID CRYSTALS

[75] Inventors: Stephen Kelly, Möhlih, Switzerland; Klaus Schmitt, Lörrach, Germany

[73] Assignee: Rolic AG, Basel, Switzerland

[21] Appl. No.: 519,228

[22] Filed: Aug. 25, 1995

[30] Foreign Application Priority Data

Aug. 31, 1994 [CH] Switzerland ............... 2666/94

[51] Int. Cl.$^6$ .................. C07C 69/76; C07C 69/90
[52] U.S. Cl. .................................... 560/66
[58] Field of Search ............................ 560/66

[56] References Cited

U.S. PATENT DOCUMENTS 5,202,053  4/1993  Shannon et al.

FOREIGN PATENT DOCUMENTS 611 981    2/1994   European Pat. Off.
4 233 660  10/1992  Germany.
WO93/22397 4/1993   WIPO.

OTHER PUBLICATIONS

Kawakami et al., Polymer International 31:35–40 (1993) "Synthesis and Thermal Transition of Side–chain Liquid Crystalline Polyoxetanes Having Laterally Attached Mesogenic Group".

Primary Examiner—Paul J. Killos
Attorney, Agent, or Firm—George W. Johnston; William H. Epstein; Lewis J. Kreisler

[57] ABSTRACT

The present invention is concerned with optically active, ferroelectric, smectic, photo-cross linkable compounds of the formula

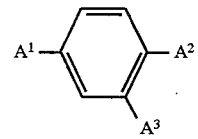

I wherein $A^1$ and $A^2$ may both signify residues of the formula

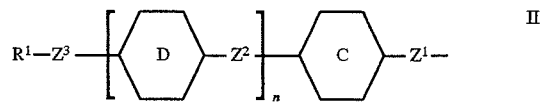

II and be the same or different, while $A^3$ may signify a residue of the formula

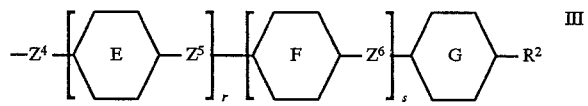

III as well as liquid crystalline mixtures which contain such compounds and their use in the cross-linked state in optical components.

18 Claims, No Drawings

OPTICALLY ACTIVE SMECTIC PHOTO-CROSS-LINKABLE LIQUID CRYSTALS

BACKGROUND

The present invention is concerned with optically active, ferroelectric, smectic photo-cross linkable liquid crystals, liquid crystalline mixtures which contain such compounds as well as their use in the cross-linked state in optical components.

Photo-cross linkable liquid crystals provided with an appropriate amount of a photoinitiator can be orientated on a substrate or in a cell by suitable orientating layers or in a field and then in this state can be cross-linked by irradiation with light of a suitable wavelength. The structure thereby produced is preserved even at high temperatures. Such layers can be, for example, parts of hybrid layers as are described in Swiss Patent Applications CH 2016/94 and CH 2017/94. Thus, optical components, such as, for example, wave guides, optical screens and filters, components having piezoelectric properties and those having non-linear optical (NLO) properties, etc., can be produced. Such optical components are used, for example, in frequency doubling (SHG).

Further properties such as, for example, the birefringence, the refractive index, transparency, etc. must fulfil different requirements depending on the field of use. For example, materials for frequency doubling (SHG) should have a strong coupling between the direction of maximum hyperpolarizability and the polar axis in order that the degree of efficiency of the signal doubling is high.

Moreover, the photo-cross linkable liquid crystals must have a good chemical and thermal stability, good solubility in usual solvents and a good stability towards electric fields and electromagnetic radiation. Furthermore, they should have a suitable mesophase from about 25° C. to about 100° C., especially from about 25° C. to about 80° C., for example they should have a broad chiral smectic mesophase for the applications referred to above.

Since liquid crystals are usually used as mixtures of several components, it is important that the components have a good miscibility with one another. Components which in mixtures bring about a frequency doubling or lead to optical activity are usually not liquid crystalline themselves. They therefore usually have the disadvantage that they lead to a large decrease of the phase transition temperatures and accordingly can be used only in low concentrations. This leads to a small SHG degree of efficiency. Mixtures consisting of photo-cross linkable liquid crystals and non-photo-cross linkable liquid crystals and/or optically active (chiral) additives permit a relaxation of the non-cross lin.kable components and thereby lead to a diminishing of the SHG signal. On the other hand, networks in which the active components are incorporated permit high concentrations of these active additives. At the same time, the orientating relaxation is prevented by the fixation in the network. Blue or green light can be produced by using in such networks colouring substances which absorb at the wavelength of the SHG light generated by a laser diode. Such networks have the disadvantage that usually they do not have sufficient long-term stability.

There is accordingly the need to produce photo-cross linkable components which satisfy the aforementioned requirements, can be structured, have an excellent thermal stability and long-term stability and a high SHG degree of efficiency.

SUMMARY

The present invention now provides compounds which are outstandingly suitable as single components or as components of such liquid crystal mixtures. These are compounds of the general formula

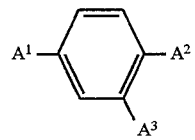

I wherein $A^1$ and $A^2$ are both residues of the formula

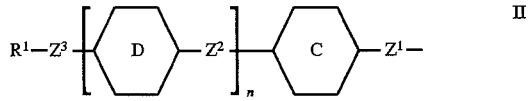

II wherein rings C and D are independently pyridine-2,5-diyl, pyrimidine-2,5-diyl, trans-1,4-cyclohexylene, trans-1,3-dioxane-2,5-diyl or 1,4-phenylene, which is optionally substituted with halogen, methyl and/or cyano;

$Z^1$ is a single bond, $-CH_2CH_2-$, $-CH_2O-$, $-COO-$, $-OOC-$, $-(CH_2)_4-$ or $-(CH_2)_3O-$;

$Z^2$ is a single bond, $-CH_2CH_2-$, $-CH_2O-$, $-OCH_2-$, $-COO-$, $-OOC-$, $-(CH_2)_4-$, $-O(CH_2)_3-$ or $-(CH_2)_3O-$;

$Z^3$ is $-(CH_2)_m-$, $-(CH_2)_mO-$, $-(CH_2)_mCOO-$ or $-(CH_2)_mOOC-$;

n is 0 or 1;

m is a whole number from 1 to 16; and $R^1$ is a cross-linkable group such as acrylate, methacrylate, 2-chloroacrylate, 2-phenylacrylate, acryloylphenylene, acrylamide, methacrylamide, 2-phenylacrylamide, epoxy, itaconic acid ester, vinyl ether, vinyl ester, styrene derivative, maleic acid derivative or fumaric acid derivative or a cinnamic acid derivative, which is optionally substituted with methyl, methoxy, cyano and/or halogen; and $A^3$ is a residue of the formula

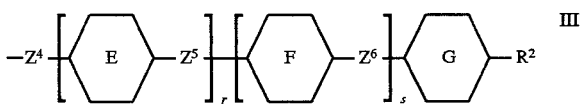

III wherein rings E and F are independently pyridine-2,5-diyl, pyrimidine-2,5-diyl, trans-1,4-cyclohexylene, trans-1,3-dioxane-2,5-diyl or 1,4-phenylene, which is optionally substituted with halogen, methyl and/or cyano;

ring G is 1,4-phenylene, which is unsubstituted or mono- or disubstituted with halogen, methyl, dimethylamino, amino, nitro and/or cyano;

$Z^4$ is a single bond, $-(CH_2)_p-$, $-(CH_2)_pO-$, $-O(CH_2)_p-$, $-(CH_2)_pCOO-$, $-OOC(CH_2)_p-$, $-(CH_2)_pOOC-$, $-COO(CH_2)p-$, $-OOC(CH_2)_pOOC-$, $-O(CH_2)_pOOC-$ or $-COO(CH_2)_pO-$;

$Z^5$, $Z^6$ each are a single bond, $-CH_2CH_2-$, $-CH_2O-$, $-OCH_2-$, $-COO-$, $-OOC-$, $-(CH_2)_4-$, $-O(CH_2)_3-$ or $-(CH_2)_3O-$;

p is a whole number from 1 to 16;

r,s each are 0 or 1; and $R^2$ is an optically active group such as (S)- or (R)-2-butyloxy, (S)- or (R)-2-pentyloxy, (S)- or (R)-2-hexyloxy, (S)- or (R)-2-heptyloxy, (S)- or (R)-2-octyloxy or alkyl, alkoxy or alkanoyloxy with 4 to 8 carbon atoms, which is substituted with methyl, methoxy, cyano and/or halogen.

DETAILED DESCRIPTION

Compounds of this invention have the general structure depicted in formula I

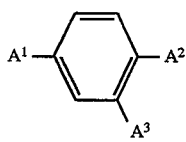

wherein $A^1$, $A^2$ each independently signify a cross-linkable mesogenic residue and $A^3$ signifies an optically active, mesogenic residue.

The mesogenic cross-linkable residues $A^1$ and $A^2$ can be different or the same. Mesogenic residues will be known to a person skilled in the art and are described, for example, in Flüssigkristalle in Tabellen, Deutscher Verlag für Grundstoffindustrie Leipzig, 1984, volume II. In order for the known mesogenic residues to be suitable for the above purpose, they are provided terminally with a polymerizable residue. The term polymerizable has its conventional meaning in that a number of reactive molecules can react in a chain reaction to form an oligomer or a polymer.

Since the compounds in accordance with the invention or compositions of their mixtures have a tilted smectic phase, they can be directed by the application of an electric field prior to the cross-linking. The pitch is thereby unwound and a uniform, ferroelectric layer is produced.

$A^1$ and $A^2$ may both signify residues of the formula

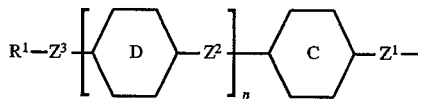

and be the same or different, while $A^3$ may signify a residue of the formula

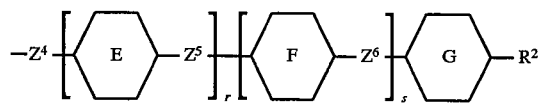

These residues have been more specifically described above.

The term cross-linkable has its conventional meaning, which is the ability to react with other polymerizable groups to form an elastomer or a network. Examples of cross-linkable groups include acrylate, methacrylate, 2-chloroacrylate, 2-phenylacrylate, acryloylphenylene, acrylamide, methacrylamide, 2-phenylacrylamide, epoxy, itaconic acid ester, vinyl ether, vinyl ester, styrene derivative, maleic acid derivative or fumaric acid derivative or a cinnamic acid derivative, which is optionally substituted with methyl, methoxy, cyano and/or halogen.

The term optically active has its conventional meaning, which is that the compound possesses a chiral carbon atom. Examples of optically active groups include (S)- or (R)-2-butyloxy, (S)- or (R)-2-pentyloxy, (S)- or (R)-2-hexyloxy, (S)- or (R)-2-heptyloxy, (S)- or (R)-2-octyloxy or alkyl, alkoxy or alkanoyloxy with 4 to 8 carbon atoms, which is substituted with methyl, methoxy, cyano and/or halogen.

The term optionally substituted in general has its conventional meaning, in that the so-described compound may or may not be substituted with one or more units of a given substituent, or with several substituents, as indicated The term single bond means a single covalent carbon-carbon bond. The phrase "from x to y" (as in a whole number from 1 to 16) as used herein is inclusive of x and y.

The term "1,4-phenylene, which is optionally substituted with halogen, methyl and/or cyano," signifies in the scope of the present invention phenylene which may have one or more halogen and/or one or more methyl and/or one or more cyano substituents, for example 1,4-phenylene, 2-fluoro-1,4-phenylene, 3-fluoro-1,4-phenylene, 2,3-difluoro-1,4-phenylene, 2-chloro-1,4-phenylene, 3-chloro-1,4-phenylene, 2,3-dichloro-1,4-phenylene, 2-cyano-1,4-phenylene, 3-cyano-1,4-phenylene, 2,3-dicyano-1,4-phenylene, 2-methyl-1,4-phenylene, 3-methyl-1,4-phenylene and the like.

The term "1,4-phenylene, which is unsubstituted or mono- or disubstituted with halogen, methyl, dimethylamino, amino, nitro and/or cyano," signifies in the scope of the present invention 1,4-phenylene or 1,4-phenylene with one or two of the substituents named above in any combination, for example, 2-amino-5-nitro-1,4-phenylene, 5-amino-2-nitro-1,4-phenylene, 2-dimethylamino-5-nitro-1,4-phenylene or 5-dimethylamino-2-nitro-1,4-phenylene and the like.

Halogen signifies the known halogens, including fluorine, chlorine, bromine and iodine, especially fluorine or chlorine.

The term "alkyl, alkoxy or alkanoyloxy with 4 to 8 carbon atoms, which is substituted with methyl, methoxy, cyano and/or halogen," signifies in the scope of the present invention optically active alkyl, alkoxy or alkanoyloxy groups. Examples of such groups are (S)- or (R)-2-methylbutyl, (S)- or (R)-2-methylpentyl, (S)- or (R)-2-methylhexyl, (S)- or (R)-2-methylheptyl, (S)- or (R)-2-methoxybutyl, (S)- or (R)-2-methoxypentyl, (S)- or (R)-2-methoxyhexyl, (S)- or (R)-2-methoxyheptyl, (S)- or (R)-1-cyanobutyl, (S)- or (R)-1-cyanopentyl, (S)- or (R)-1-cyanohexyl, (S)- or (R)-1-cyanoheptyl, (S)- or (R)-2-cyanobutyl, (S)- or (R)-2-cyanopentyl, (S)- or (R)-2-cyanohexyl, (S)- or (R)-2-cyanoheptyl, (S)- or (R)-1-fluorobutyl, (S)- or (R)-1-fluoropentyl, (S)- or (R)-1-fluorohexyl, (S)- or (R)-1-fluoroheptyl, (S)- or (R)-2-fluorobutyl, (S)- or (R)-2-fluoropentyl, (S)- or (R)-2-fluorohexyl, (S)- or (R)-2-fluoroheptyl, (S)- or (R)-1-chlorobutyl, (S)- or (R)-1-chloropentyl, (S)- or (R)-1-chlorohexyl, (S)- or (R)-1-chloroheptyl, (S)- or (R)-2-chlorobutyl, (S)- or (R)-2-chloropentyl, (S)- or (R)-2-chlorohexyl or (S)- or (R)-2-chloroheptyl and the like.

The term derivatives, used in connection with styrene, and maleic, fumaric, and cinnamic acid has its conventional meaning. Specifically, derivative means a reaction product thereof as for example an ester or an amid. The cinnamic acid derivative may be substituted with one or more of the following substituents in any combination: methyl, methoxy, cyano, and halogen.

Preferred compounds of formula I are compounds of the general formula

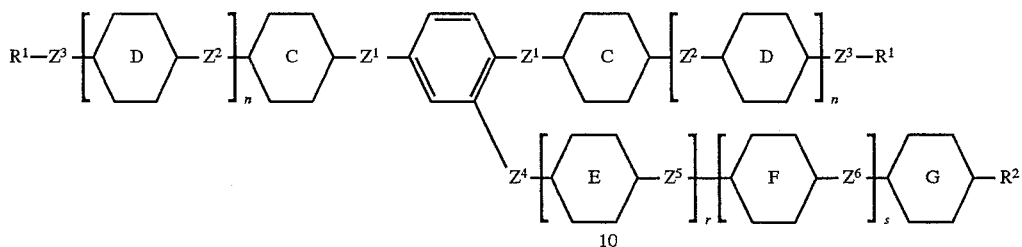

I-1

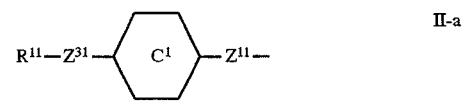

wherein the symbols are as defined above in connection with formula I, II, and III.

The mesophase type of the compounds of formula I-1 in accordance with the invention can be influenced by varying rings C, D, E and F. Thus, aromatic rings are more inclined to produce smectic phases. Therefore in preferred compounds of this invention, for example a compound of formula I, where $A^1$ and $A^2$ are residues of formula II and A3 is a residue of formula III, or in particular a compound of formula I-1, rings C-G, $Z^1$ and $Z^2$, and $R^1$ and $R^2$ are as defined below.

Rings C and D each independently signify 1,4-phenylene, 2-fluoro-1,4-phenylene, 3-fluoro-1,4-phenylene, pyridine-2,5-diyl or pyrimidine-2,5-diyl, especially 1,4-phenylene, 2-fluoro-1,4-phenylene or 3-fluoro-1,4-phenylene. Rings E and F preferably signify 1,4-phenylene, while ring G preferably signifies 2-amino-5-nitro-1,4-phenylene or 5-amino-2-nitro-1,4-phenylene.

Especially preferred are compounds in which $Z^1$ signifies —$CH_2O$—, —COO— or —OOC—; and $Z^2$ signifies a single bond, —$CH_2CH_2$—, —$CH_2O$—, —$OCH_2$—, —COO— or —OOC—.

In especially preferred compounds the residue $R^1$ signifies acrylate, methacrylate, 2-chloroacrylate, 2-phenylacrylate, acryloylphenylene, acrylamide, methacrylamide, 2-phenylacrylamide, epoxy, vinyl ether, vinyl ester, styrene derivative, maleic acid derivative or fumaric acid derivative and the like. These are thus residues which can be cross-linked photochemically after orientation of the compounds of formula I in a field. Acrylate, methacrylate, vinyloxy and epoxy are especially preferred residues $R^1$.

(S)- or (R)-2-Butyloxy, (S)- or (R)-2-pentyloxy, (S)- or (R)-2-hexyloxy, (S)- or (R)-2-heptyloxy and (S)- or (R)-2-octyloxy are preferably used as optically active residues $R^2$.

Thus, a compound of formula I of this invention, such as a compound where $A^1$ and $A^2$ are residues of formula II and $A^3$ is a residue of formula III, or in particular a compound of formula I-1 of this invention, may be characterized by having any one or more of the following characteristics: rings C and D independently signifying 1,4-phenylene, 2-fluoro-1,4-phenylene, 3-fluoro-1,4-phenylene, pyridine-2,5-diyl or pyrimidine-2,5-diyl, (especially 1,4-phenylene, 2-fluoro-1,4-phenylene or 3-fluoro-1,4-phenylene), and/or rings E and F signifying 1,4-phenylene, and/or ring G signifying 2-amino-5-nitro-1,4-phenylene or 5-amino-2-nitro-1,4-phenylene, and/or $Z_1$ signifying —$CH_2O$—, —COO— or —OOC—, and/or $Z^2$ signifying a single bond, —$CH_2CH_2$—, —$CH_2O$—, —$OCH_2$—, —COO— or —OOC—, and/or $R^1$ signifying acrylate, methacrylate, 2-chloroacrylate, 2-phenylacrylate, acryloylphenylene, acrylamide, methacrylamide, 2-phenylacrylamide, epoxy, vinyl ether, vinyl ester, styrene derivative, maleic acid derivative or fumaric acid derivative, (especially, acrylate, methacrylate, vinyloxy and epoxy), and/or $R^2$ signifying (S)- or (R)-2-Butyloxy, (S)- or (R)-2-pentyloxy, (S)- or (R)-2-hexyloxy, (S)- or (R)-2-heptyloxy and (S)- or (R)-2-octyloxy. Remaining symbols are as defined above.

Preferably, the mesogenic residues $A^1$ and $A^2$ are the same and signify a residue of formula II in which n=0 such as, for example II-a $R^{11}$—$Z^{31}$—⟨$C^1$⟩—$Z^{11}$— wherein $R^{11}$ signifies acrylate, methacrylate or epoxy;

$Z^{31}$ signifies —$(CH_2)_t$—, —$(CH_2)_tO$—, —$(CH_2)_tCOO$— or —$(CH_2)_tOOC$—;

t signifies a whole number from 4 to 12;

ring $C^1$ signifies 1,4-phenylene, 2-fluoro-1,4-phenylene or 3-fluoro-1,4-phenylene; and $Z^{11}$ signifies —$CH_2O$—, —COO— or —OOC—.

Preferably, the mesogenic residue $A^3$ signifies a residue of formula III such as, for example

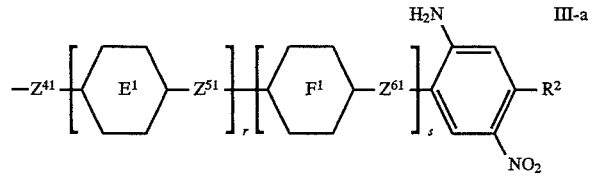

III-a wherein $R^2$ signifiess (S)- or (R)-2-butyloxy, (S)- or (R)-2-pentyloxy, (S)- or (R)-2-hexyloxy, (S)- or (R)-2-heptyloxy or (S)- or (R)-2-octyloxy;

r,s signify 0 or 1;

$Z^{41}$ signifies —$CH_2CH_2CH_2$—, —$OCH_2CH_2$—, —$CH_2CH_2O$—, —$COOCH_2$— or —$CH_2OOC$—;

$Z^{51}$, $Z^{61}$ signify a single bond, —$CH_2CH_2$—, —$CH_2O$—, —COO—, —OOC, —$(CH_2)_4$— or —$(CH_2)_3O$—; and rings $E^1$ and $F^1$ signify 1,4-phenylene.

Quite particularly preferred compounds of formula I-1 are therefore the compounds of the formula

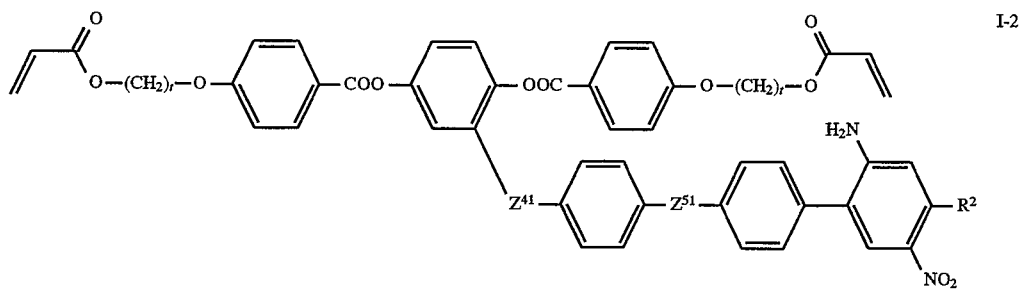

I-2 wherein t is a whole number from 4 to 12;

$R^2$ signifies (S)- or (R)-2-butyloxy, (S)- or (R)-2-pentyloxy, (S)- or (R)-2-hexyloxy, (S)- or (R)-2-heptyloxy or (S)- or (R)-2-octyloxy;

$Z^{41}$ signifies —COOCH$_2$—; and $Z^{51}$ signifies a single bond, —COO— or —OOC—.

Especially preferred compounds of formula I-1 are (4-[4-(2-amino-5-nitro-4-[(S)-2-octyloxy]phenyl) benzoyloxy]phenyl)methyl 2,5-bis(4-[6-acryloyloxyhexyloxy]phenylcarboxy) benzoate, (4-[4-(2-amino-5-nitro-4-[(S)-2-octyloxy]phenyl)benzoyloxy]phenyl)methyl 2,5-bis(4-[11-acryloyloxyhexyloxy]phenylcarboxy)benzoate, and 4-[4-(2-amino-5-nitro-4-[(S)-2-octyloxy]phenyl)benzoyloxy]butyl 2,5-bis (4-[11-acryloyloxyundecyloxy]phenylcarboxy) benzoate.

The compounds of general formula I in accordance with the invention are very readily accessible synthetically and can be produced in a manner known per se by conventional methods, for example analogously to the methods illustrated in Schemes 1 and 2 as well as in the Examples.

The mesogenic residues of formula II and III are known or are analogues of known structures and can be prepared in a manner known per se and subsequently linked with the aromatics.

A small amount of BHT (2,6-di-tert.-butyl-4-methylphenol="butylhydroxytoluene") is admixed in each step in order to stop undesired thermal cross-linkage.

In the Schemes the symbols are as described above.

Scheme 1

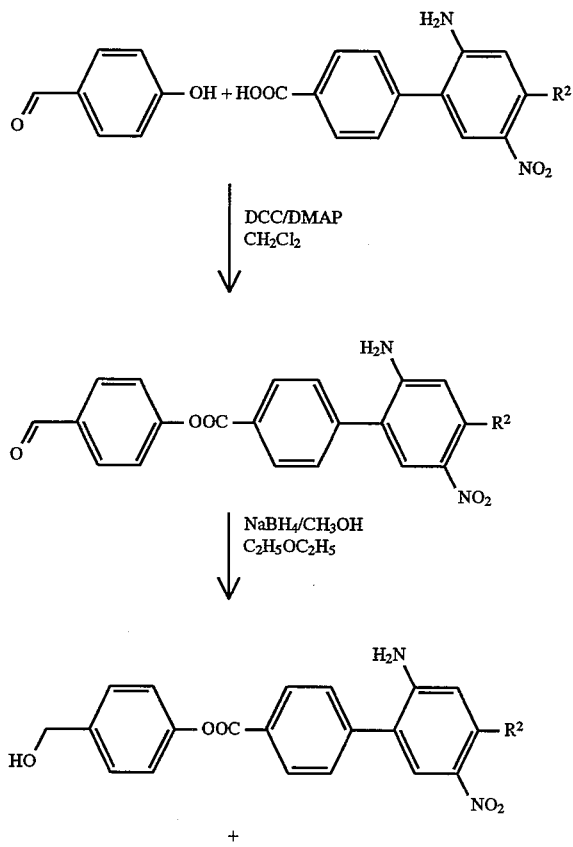

+

-continued
Scheme 1
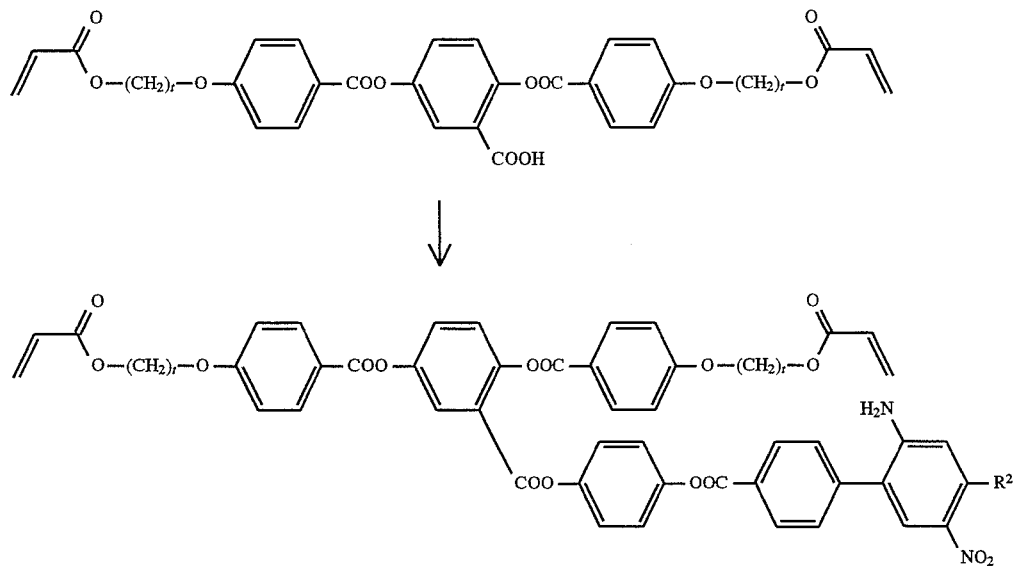
Scheme 2
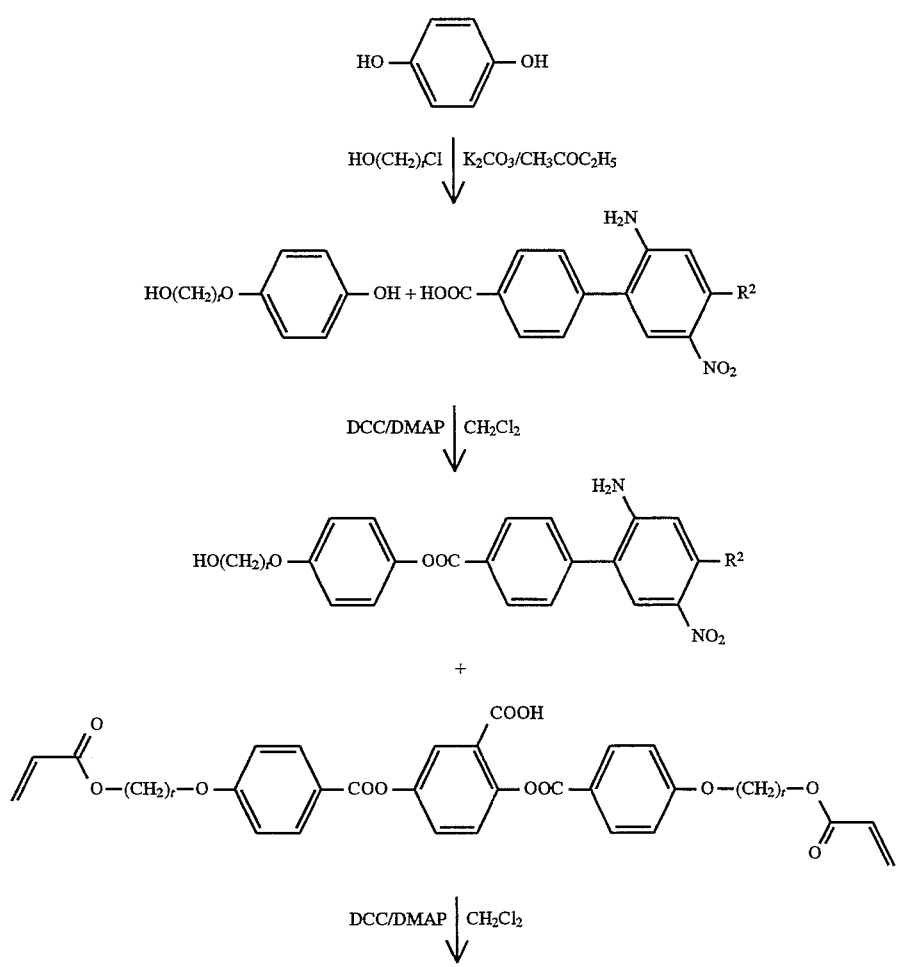

-continued
Scheme 2

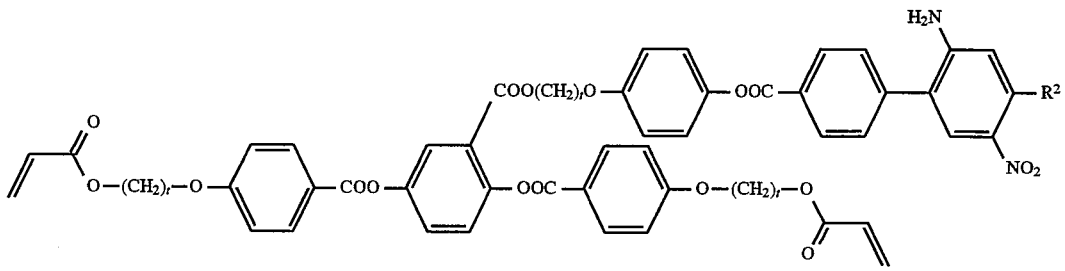

The compounds of this invention may be prepared by conventional methods using known starting materials, are readily accessible synthetically and can be produced, for example, in a manner known per se from optically active alcohols (derivatives of formula III) and bis[2,5-bis(4-[n-acryloyloxyalkyloxy)]-phenylcarboxy)benzoic acids. The esterification can be effected, for example, in the presence of N,N'-dicyclohexylcarbodiimide (DCC) and 4-(dimethylamino)pyridine (DMAP) in dichloromethane or another suitable solvent such as e.g. chloroform.

Further, compounds of formula I can be produced by firstly etherifying 4-benzaldehyde with ω-halo-1-alcohol derivatives, reducing the aldehyde with sodium borohydride to the benzyl alcohol derivative of formula II, etherifying this derivative with 2,5-dihydoxybenzaldehyde in a Mitsonobu reaction, then esterifying with acrylic acid, oxidizing to the corresponding benzoic acid with Jones' reagent and subsequently esterifying with optically active alcohols (derivatives of formula III) as described above.

The optically active alcohols (derivatives of formula III), for example, from the esterification product of 4-hydroxybenzaldehyde with 4-[4-(2-amino-5-nitro-4-[(S)-2-alkyloxy]phenyl)-benzoic acids by reduction with sodium borohydride.

Asymmetric compounds, i.e. compounds in which residue $A^1$ and residue $A^2$ have different formulae, can be prepared by conventional methods from available materials, for example by mono-esterifying 2,5-dihydroxybenzaldehyde with a 4-(n-acryloyloxyalkyloxy)benzoic acid to the monoester and them again esterifying with another 4-(n-acryloyloxyalkyloxy)benzoic acid to the diester. Oxidation of this diester with Jones' reagent gives the corresponding asymmetric [2,5-bis(4-[n-acryloyloxyalkyloxy)]-phenylcarboxy)benzoic acid which is subsequently reacted with an alcohol (derivative of formula III). The starting materials are known and can be prepared or in some cases obtained commercially.

The compounds of this invention can be used as single compounds or in the form of mixtures with one another and/or with other liquid crystal components.

The liquid crystalline mixtures in accordance with the invention contain at least two components, of which at least one component is a compound of this invention, for example a compound of formula I, or a compound of formula I where $A^1$ and $A^2$ are both residues of formula II and $A^3$ is a residue of formula III, or any other compound of this invention. A second component and optionally additional components can be compounds of this invention or other known liquid crystalline compounds having photo-cross linkable groups. Additional chiral components can also be present in the mixture.

Having regard to the good solubility of the compounds of formula I and having regard to their good miscibility with one another, the content of different compounds of formula I in the mixtures in accordance with the invention can be high and can amount to 100 wt. %. The compounds in the mixture may thus be present in any proportion which provides a sufficiently high second harmonic signal intensity before and after polymerization in the ferroelectric chiral smectic C phase. The properties can for example be determined as described in Appl. Phys. B59, 607–615, 1994 and J. Phys. III (Paris) 4, 387–400, 1994.

The mixtures in accordance with the invention preferably contain, in addition to one or more compounds of formula I, one or more compounds from the group of compounds of the general formulae

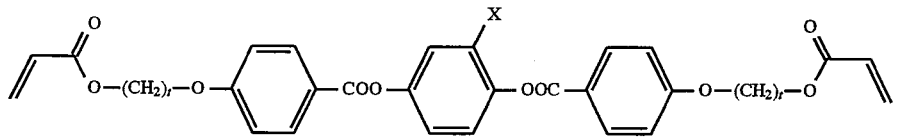   V

-continued
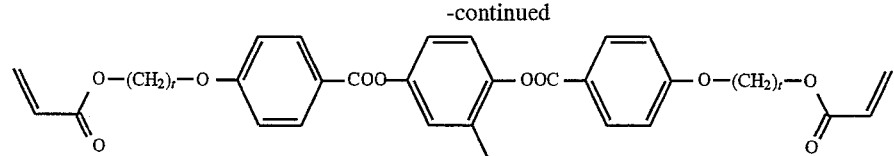
VI
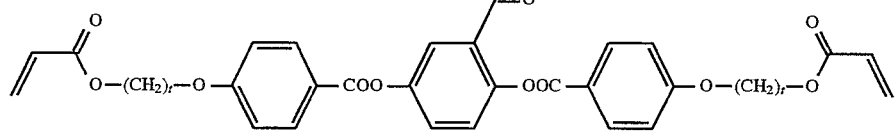
VII
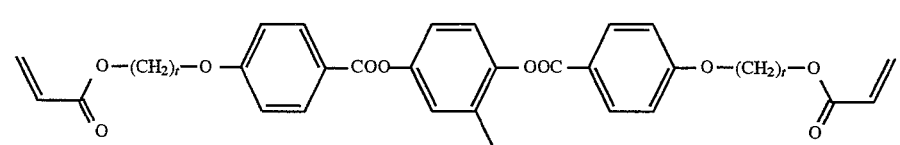
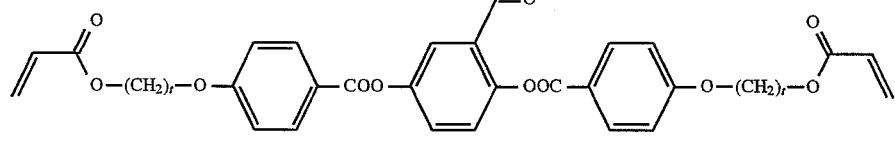
VIII
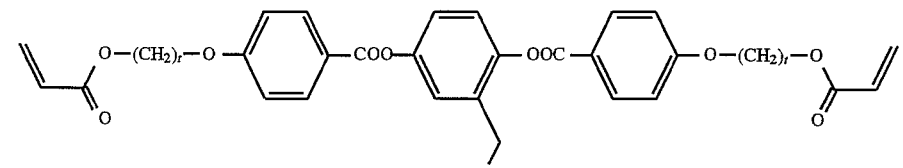
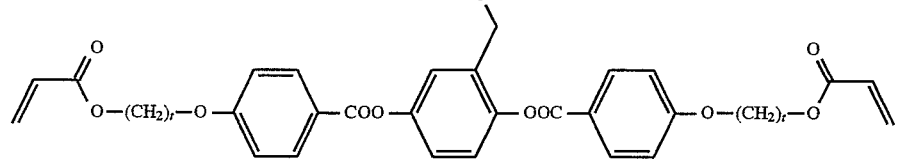

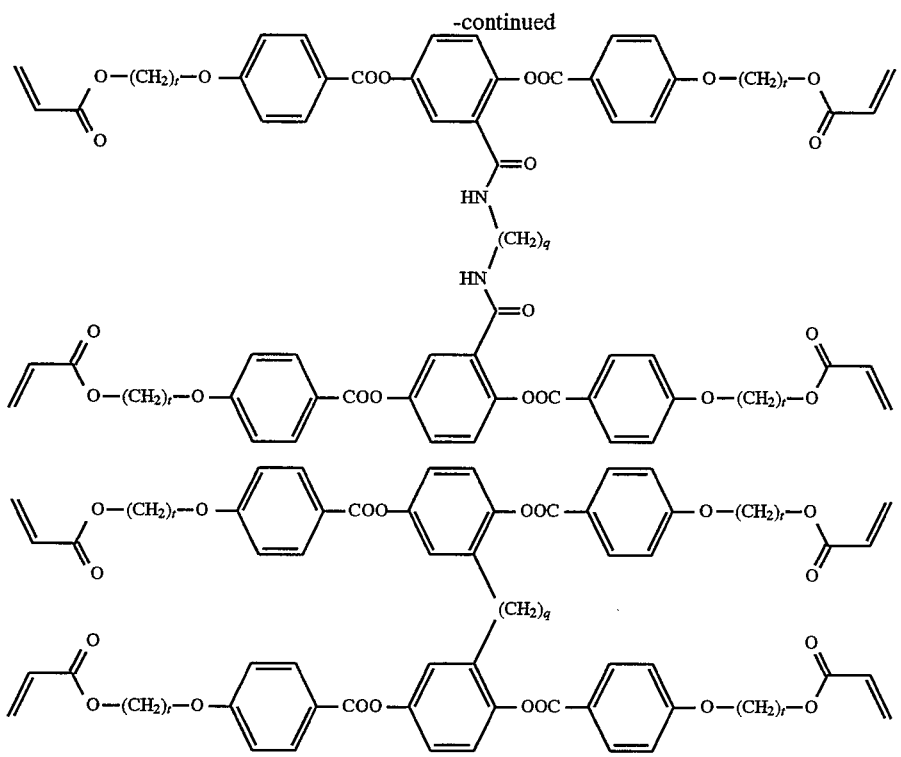

wherein t signifies a whole number from 4 to 12 and q signifies a whole number from 2 to 12.

The compounds of formula V are well known in the art and are described in Mol. Makromol. Chem. 190, 2255, 1989 and 190, 3201, 1989. The compounds of formulae VI through X are well known in the art and can be obtained by conventional methods as described in Swiss Patent Application 953/94. The compositions of this invention are mixtures of at least one compound of this invention such as a compound of formula I where $A^1$ and $A^2$ are residues of formula II and $A^3$ is a residue of formula III, and at least compound selected from the compounds of formulae V through X. Specific compositions of this invention include a mixture of a compound of formula I where $A^1$ and $A^2$ are residues of formula II and $A^3$ is a residue of formula III, with individually a compound of formula V, or VI, or VII, or VIII, or IX, or X.

The production of the compounds of this invention as well as liquid crystalline mixtures containing these compounds are illustrated in more detail by the following Examples. C signifies a crystalline phase, S signifies a smectic phase, N* signifies the chiral nematic phase and I signifies the isotropic phase. "ac" signifies alternating current and "dc" signifies direct current. Optical antipodes have in each case "mirror image properties", i.e. the same melting point etc., but lead to opposite helical rotation and opposite circular polarization of the reflected light.

EXAMPLE 1

0.2 g of N,N'-dicyclodicyclohexylcarbodiimide was added at room temperature while stirring to a solution of 0.6 g of 2,5-bis(4-[6-acryloyloxyhexyloxy]phenylcarboxy)benzoic acid, 0.4 g of 4-[4-(2-amino-5-nitro-4-[(S)-2-octyloxy]-phenyl)benzoyloxy]phenylmethanol and 0.04 g of 4-dimethylaminopyridine in 20 ml of dichloromethane. The reaction mixture was stirred at room temperature overnight, poured into 100 ml of water and then extracted three times with 50 ml of dichloromethane each time. The organic phases were washed twice with 100 ml of water each time, dried over magnesium sulphate, filtered and subsequently concentrated. Chromatographic purification of the residue on silica gel with hexane/ethyl acetate (vol. 1:1) and twofold recrystallization from acetone of the fractions which were pure according to thin-layer chromatography gave 0.4 g of (4-[4-(2-amino-5-nitro-4-[(S)-2-octyloxy]phenyl)benzoyloxy]phenyl)-methyl 2,5-bis(4-[6-acryloyloxyhexyloxy]phenylcarboxy)benzoate; m.p. (C-I) 100° C., Sc*-N*, 96° C., cl.p. (N*-I) 100° C.

The (4-[4-(5-amino-2-nitro-4-[(S)-2-octyloxy]phenyl)-benzoyloxy]phenyl)methanol used as the starting material was prepared as follows:

a) A mixture of 0.13 g of sodium borohydride and 15 ml of water was treated dropwise at 0° C. with a solution of 0.8 g of 4-[4 -(2-amino-5-nitro-4-[(S)-2-octyloxy]phenyl)benzoyloxy]benzaldehyde in 100 ml of dioxan. The reaction mixture was stirred at 0° C. for a further 60 minutes and then at room temperature for 10 minutes and thereafter poured into 100 ml of dichloromethane. The organic phase was separated and washed twice with 100 ml of water each time. The aqueous phases were extracted twice with 50 ml of dichloromethane each time. The combined organic phases were then washed twice with 100 ml of water each time, dried over magnesium sulphate, the suspension was filtered and the filtrate was concentrated. The residue was used in the next step without further purification.

b) 0.6 g of N,N'-dicyclodicyclohexylcarbodiimide was added at room temperature while stirring to a solution of 1.0 g of 4-[4-(2-amino-5-nitro-4-[(S)-2-octyloxy]phenyl)benzoic acid, 0.3 g of 4-hydroxybenzaldehyde and 0.04 g of 4-dimethylaminopyridine in 20 ml of dichloromethane. The reaction mixture was stirred at room temperature overnight, poured into 100 ml of water and then extracted three times with 50 ml of dichloromethane each time. The organic phases were washed twice with 100 ml of water each time, dried over magnesium sulphate, filtered and the filtrate was subsequently concentrated. Chromatographic purification of the residue on silica gel with hexane/ethyl acetate (vol. 1:1) and two-fold recrystallization from ethanol of the fractions which were pure according to thin-layer chromatography gave 0.9 g of 4-[4-(2-amino-5-nitro-4-[(S)-2-octyloxy] phenyl)benzoyloxy]benzaldehyde; m.p. (C-I) 77°–78° C.

The following compounds can be produced in an analogous manner:

(4-[4-(2-Amino-5-nitro-4-[(S)-2-octyloxy]phenyl) benzoyloxy]phenyl)methyl 2,5-bis(4-[7-acryloyloxyheptyloxy]phenylcarboxy)benzoate.

(4-[4-(2-Amino-5-nitro-4-[(S)-2-octyloxy]phenyl) benzoyloxy]phenyl)methyl 2,5-bis(4-[8-acryloyloxyoctyloxy]phenylcarboxy)benzoate.

(4-[4-(2-Amino-5-nitro-4-[(S)-2-octyloxy]phenyl) benzoyloxy]phenyl)methyl 2,5-bis(4-[9-acryloyloxynonyloxy]phenylcarboxy)benzoate.

(4-[4-(2-Amino-5-nitro-4-[(S)-2-octyloxy]phenyl) benzoyloxy]phenyl)methyl 2,5-bis(4-[10-acryloyloxydecyloxy]phenylcarboxy)benzoate.

(4-[4-(2-Amino-5-nitro-4-[(S)-2-octyloxy]phenyl) benzoyloxy]phenyl)methyl 2,5-bis(4-[11-acryloyloxyundecyloxy]phenylcarboxy)benzoate; m.p. (C-$S_A$) 108° C.; cl.p. ($S_A$-I) 112° C.

(4-[4-(2-Amino-5-nitro-4-[(S)-2-octyloxy]phenyl) benzoyloxy]phenyl)methyl 2,5-bis(4-[12-acryloyloxydodecyloxy]phenylcarboxy)benzoate.

[4-(2-Amino-5-nitro-4-[(S)-2-octyloxy]benzoyloxy) phenyl]methyl 2,5-bis(4-[7-acryloyloxyheptyloxy] phenylcarboxy) benzoate.

[4-(2-Amino-5-nitro-4-[(S)-2-octyloxy]benzoyloxy) phenyl]methyl 2,5-bis(4-[8-acryloyloxyoctyloxy] phenylcarboxy)benzoate.

[4-(2-Amino-5-nitro-4-[(S)-2-octyloxy]benzoyloxy) phenyl]methyl 2,5-bis(4-[9-acryloyloxynonyloxy] phenylcarboxy)benzoate.

[4-(2-Amino-5-nitro-4-[(S)-2-octyloxy]benzoyloxy) phenyl]methyl 2,5-bis(4-[10-acryloyloxydecyloxy] phenylcarboxy)benzoate.

[4-(2-Amino-5-nitro-4-[(S)-2-octyloxy]benzoyloxy) phenyl]methyl 2,5 -bis(4-[11-acryloyloxyundecyloxy] phenylcarboxy)benzoate.

[4-(2-Amino-5-nitro-4-[(S)-2-octyloxy]benzoyloxy) phenyl]methyl 2,5-bis(4-[12-acryloyloxydodecyloxy] phenylcarboxy)benzoate.

EXAMPLE 2

0.6 g of 2,5-bis (4-[6-acryloyloxyhexyloxy] phenylcarboxy)benzoic acid and 0.4 g of (4-[4-(2-amino-5-nitro-4-[(S)-2-octyloxy]phenyl)benzoyloxy]phenoxy) ethanol, 0.04 g of 4-dimethylaminopyridine, 0.2 g N,N'-dicyclodicyclohexyldicarbodiimide and 20 ml of dichloromethane are reacted in an analogous manner to Example 1 to give (4-[4-(2-amino-5-nitro-4-[(S)-2-octyloxy]-phenyl)benzoyloxy]phenoxy)ethyl 2,5-bis (4-[6-acryloyloxyhexyloxy]phenylcarboxy)benzoate.

The (4-[4-(2-amino-5-nitro-4-[(S)-2-octyloxy]phenyl) benzoyloxy]phenoxy)ethanol used as the starting material is prepared as follows:

a) 0.6 g of 4-[4-(2-amino-5-nitro-4-[(S)-2-octyloxy] phenyl)benzoic acid and 0.2 g of (4-hydroxyphenoxy) ethanol, 0.04 g of 4-dimethylaminopyridine, 0.4 g of N,N'-dicyclodicyclohexyldicarbodiimide and 50 ml of dichloromethane are reacted in an analogous manner to Example 1 to give 0.4 g of (4-[4-(2-amino-5-nitro-4-[(S)-2-octyloxy]phenyl)benzoyloxy]phenoxy)ethanol.

b) A solution of 5.0 g of 4-hydroquinone and 3.7 g of chloroethanol in 50 ml of ethyl methyl ketone is treated with 25 g of finely powdered potassium carbonate and the mixture is heated under slight reflux overnight. The suspension is suction filtered and the filtrate is concentrated in a vacuum. A solution of the residue in 100 ml of diethyl ether is washed twice with 100 ml of water each time, dried over sodium sulphate and concentrated. Chromatography of the crude product on silica gel with hexane/ethyl acetate (vol. 7:3) gives 2.0 g of (4-hydroxyphenoxy)ethanol.

The following compounds can be produced in an analogous manner:

(4-[4-(2-Amino-5-nitro-4-[(S)-2-octyloxy]phenyl) benzoyloxy]phenoxy)ethyl 2,5-bis(4-[7-acryloyloxyheptyloxy]phenylcarboxy)benzoate.

(4-[4-(2-Amino-5-nitro-4-[(S)-2-octyloxy]phenyl) benzoyloxy]phenoxy)ethyl 2,5-bis(4-[8-acryloyloxyoctyloxy]phenylcarboxy)benzoate.

(4-[4-(2-Amino-5-nitro-4-[(S)-2-octyloxy]phenyl) benzoyloxy]phenoxy)ethyl 2,5-bis(4-[9-acryloyloxynonyloxy]phenylcarboxy)benzoate.

(4-[4-(2-Amino-5-nitro-4-[(S)-2-octyloxy]phenyl) benzoyloxy]phenoxy)ethyl 2,5-bis (4-[10-acryloyloxydecyloxy]phenylcarboxy)benzoate.

(4-[4-(2-Amino-5-nitro-4-[(S)-2-octyloxy]phenyl) benzoyloxy]phenoxy)ethyl 2,5-bis(4- [11-acryloyloxyundecyloxy]phenylcarboxy)benzoate.

(4-[4-(2-Amino-5-nitro-4-[(S)-2-octyloxy]phenyl) benzoyloxy]phenoxy)ethyl 2,5-bis (4-[12-acryloyloxydodecyloxy]phenylcarboxy)benzoate.

[4-(2-Amino-5-nitro-4-[(S)-2-octyloxy]benzoyloxy) phenoxy)]ethyl 2,5-bis(4-[7-acryloyloxheptyloxy] phenylcarboxy)benzoate.

[4-(2-Amino-5-nitro-4-[(S)-2-octyloxy]benzoyloxy) phenoxy)]ethyl 2,5-bis(4-[8-acryloyloxyoctyloxy] phenylcarboxy)benzoate.

[4-(2-Amino-5-nitro-4-[(S)-2-octyloxy]benzoyloxy) phenoxy)]ethyl 2,5-bis(4-[9-acryloyloxynanyloxy] phenylcarboxy)benzoate.

[4-(2-Amino-5-nitro-4-[(S)-2-octyloxy]benzoyloxy)-phenoxy)]ethyl 2,5-bis(4-[10-acryloyloxydecyloxy] phenylcarboxy)benzoate.

[4-(2-Amino-5-nitro-4-[(S)-2-octyloxy]benzoyloxy) phenoxy]ethyl 2,5-bis(4-[11-acryloyloxyundecyloxy] phenylcarboxy)benzoate.

[4-(2-Amino-5-nitro-4-[(S)-2-octyloxy]benzoyloxy) phenoxy)]ethyl 2,5-bis(4-[12-acryloyloxydodecyloxy] phenylcarboxy)benzoate.

EXAMPLE 3

0.3 g of 4-[4-(2-amino-5-nitro-4-[(S)-2-octyloxy]phenyl) benzoic acid, 0.8 g of 4-hydroxybutyl 2,5-bis(4-[11-acryloyloxyundecyloxy]phenylcarboxy)benzoate and 0.04 g of 4 -dimethylaminopyridine, 0.2 g N,N'-dicyclodicyclohexyldicarbodiimide and 50 ml of dichloromethane are reacted in an analogous manner to Example 1 to give 0.5 g of 4-[4-(2-amino-5-nitro-4-[(S)-2-octyloxy] phenyl)benzoyloxy]butyl 2,5-bis(4-[11-acryloyloxyundecyloxy]phenylcarboxy) benzoate.

The 4-hydroxybutyl 2,5-bis(4-[11-acryloyloxyundecyloxy]phenylcarboxy)benzoate used as the starting material is prepared as follows:

(a) 1.0 g of 2,5-bis(4-[11-acryloyloxyundecyloxy] phenylcarboxy)benzoic acid and 1.0 g of 1,4-butanediol, 0.04 g of 4-dimethylaminopyridine, 0.4 g of N,N'-dicyclodicyclohexyldicarbodiimide and 50 ml of dichloromethane are reacted in an analogous manner to Example 1 to give 0.8 g of 4-hydroxybutyl 2,5-bis(4-[11-acryloyloxyundecyloxy]phenylcarboxy) benzoate.

The following compounds can be produced in an analogous manner:

3-[4-(2-Amino-5-nitro-4-[(S)-2-octyloxy]phenyl) benzoyloxy]propyl 2,5-bis(4-[11-acryloyloxyundecyloxy] phenylcarboxy)benzoate;

5-[4-(2-amino-5-nitro-4-[(S)-2-octyloxy]phenyl) benzoyloxy]pentyl 2,5-bis(4-[11-acryloyloxyundecyloxy] phenylcarboxy)benzoate;

6-[4-(2-amino-5-nitro-4-[(S)-2-octyloxy]phenyl) benzoyloxy]hexyl 2,5-bis(4-[11-acryloyloxyundecyloxy] phenylcarboxy)benzoate;

7-[4-(2-amino-5-nitro-4-[(S)-2-octyloxy]phenyl) benzoyloxy]propyl 2,5-bis(4-[11-acryloyloxyundecyloxy] phenylcarboxy)benzoate;

8-[4-(2-amino-5-nitro-4-[(S)-2-octyloxy]phenyl) benzoyloxy]octyl 2,5-bis(4-[11-acryloyloxyundecyloxy] phenylcarboxy)benzoate;

9-[4-(2-amino-5-nitro-4-[(S)-2-octyloxy]phenyl) benzoyloxy]nonyl 2,5-bis(4-[11-acryloyloxyundecyloxy] phenylcarboxy)benzoate;

10-[4-(2-amino-5-nitro-4-[(S)-2-octyloxy]phenyl) benzoyloxy]decyl 2,5-bis(4-[11-acryloyloxyundecyloxy] phenylcarboxy)benzoate;

11-[4-(2-amino-5-nitro-4-[(S)-2-octyloxy]phenyl) benzoyloxy]undecyl 2,5-bis(4-[11-acryloyloxyundecyloxy] phenylcarboxy)benzoate;

12-[4-(2-amino-5-nitro-4-[(S)-2-octyloxy]phenyl) benzoyloxy]dodecyl 2,5-bis(4-[11-acryloyloxyundecyloxy] phenylcarboxy)benzoate;

3-[4-(2-amino-5-nitro-4-[(S)-2-octyloxy]phenyl) benzoyloxy]propyl 2,5-bis(4-[5-acryloyloxypentyloxy] phenylcarboxy)benzoate;

3-[4-(2-amino-5-nitro-4-[(S)-2-octyloxy]phenyl) benzoyloxy]propyl 2,5-bis(4-[6-acryloyloxyhexyloxy] phenylcarboxy)benzoate;

3-[4-(2-amino-5-nitro-4-[(S)-2-octyloxy]phenyl) benzoyloxy]propyl 2,5-bis(4-[7-acryloyloxyheptyloxy] phenylcarboxy)benzoate;

3-[4-(2-amino-5-nitro-4-[(S)-2-octyloxy]phenyl) benzoyloxy]propyl 2,5-bis(4-[8-acryloyloxyoctyloxy] phenylcarboxy)benzoate;

3-[4-(2-amino-5-nitro-4-[(S)-2-octyloxy]phenyl) benzoyloxy]propyl 2,5-bis(4-[9-acryloyloxynonyloxy] phenylcarboxy)benzoate;

3-[4-(2-amino-5-nitro-4-[(S)-2-octyloxy]phenyl) benzoyloxy]propyl 2,5-bis(4-[10-acryloyloxydecyloxy] phenylcarboxy)benzoate;

EXAMPLE 4

A mixture (I-N*, 114° C., N*-Sc* 106° C. and Sc*-Sx 70° C.) of 0.05 g of 4-[4-(5-amino-2-nitro-4-[(S)-2-octyloxy] phenyl)benzoyloxy]-phenylmethyl 2,5-bis(4-[6-acryloyloxyhexyloxy]phenylcarboxy)benzoate and 0.20 g of 2,5-bis(4-[6-acryloyloxyhexyloxy]-phenylcarboxy) benzoate provided with 6 μm spacer was treated with 3 wt. % of a photoinitiator (Irgacure, Ciba Geigy) and 1 wt. % of BHT and filled at 160° C. into a 7.8 μm cell with parallel orientation. The layer was orientated at 105° C. in an electric field (15 V ac), then the helix was wound up at 90° C. and at 110 V dc and illuminated in this state with xenon light (e.g. for 15 minutes). This layer functions as a frequency doubler.

We claim:

1. A compound of formula

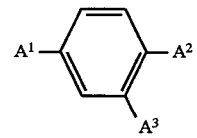

I wherein $A^1$ and $A^2$ are both residues of the formula

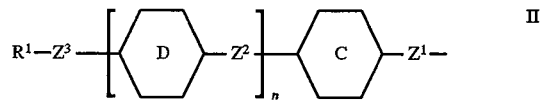

II wherein rings C and D are independently pyridine-2,5-diyl, pyrimidine-2,5-diyl, trans-1,4-cyclohexylene, trans-1,3-dioxane-2,5-diyl or 1,4-phenylene, which is optionally substituted with halogen, methyl and/or cyano;

$Z^1$ is a single bond, —$CH_2CH_2$—, —$CH_2O$—, —COO—, —OOC—, —$(CH_2)_4$— or —$(CH_2)_3O$—;

$Z^2$ is a single bond, —$CH_2CH_2$—, —$CH_2O$—, —$OCH_2$—, —COO—, —OOC—, —$(CH_2)_4$—, —$O(CH_2)_3$— or —$(CH_2)_3O$—;

$Z^3$ is —$(CH_2)_m$—, —$(CH_2)_mO$—, —$(CH_2)_mCOO$— or —$(CH_2)_mOOC$—;

n is 0 or 1;

m is a whole number from 1 to 16; and $R^1$ is a cross-linkable group such as acrylate, methacrylate, 2-chloroacrylate, 2-phenylacrylate, acryloylphenylene, acrylamide, methacrylamide, 2-phenylacrylamide, epoxy, itaconic acid ester, vinyl ether, vinyl ester, styrene derivative, maleic acid derivative or fumaric acid derivative or a cinnamic acid derivative, which is optionally substituted with methyl, methoxy, cyano and/or halogen; and $A^3$ is a residue of the formula

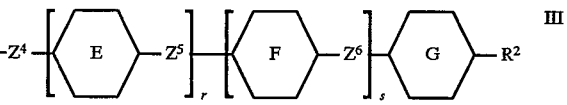

III wherein rings E and F are independently pyridine-2,5-diyl, pyrimidine-2,5-diyl, trans-1,4-cyclohexylene, trans-1,3-dioxane-2,5-diyl or 1,4-phenylene, which is optionally substituted with halogen, methyl and/or cyano;

ring G is 1,4-phenylene, which is unsubstituted or mono- or disubstituted with halogen, methyl, dimethylamino, amino, nitro and/or cyano;

$Z^4$ is a single bond, —$(CH_2)_p$—, —$(CH_2)_pO$—, —$O(CH_2)_p$—, —$(CH_2)_pCOO$—, —$OOC(CH_2)_p$—, —$(CH_2)_pOOC$—, —$COO(CH_2)p$—, —$OOC(CH_2)_pOOC$—, —$O(CH_2)_pOOC$— or —$COO(CH_2)_pO$—;

$Z^5$, $Z^6$ each are a single bond, —$CH_2CH_2$—, —$CH_2O$—, —$OCH_2$—, —COO—, —OOC—, —$(CH_2)_4$—, —$O(CH_2)_3$— or —$(CH_2)_3O$—;

p is a whole number from 1 to 16;

r,s each are 0 or 1; and $R^2$ is an optically active group such as (S)- or (R)-2-butyloxy, (S)- or (R)-2-pentyloxy, (S)- or (R)-2- hexyloxy, (S)- or (R)-2-heptyloxy, (S)- or (R)-2-octyloxy or alkyl, alkoxy or alkanoyloxy with 4 to 8 carbon atoms, which is substituted with methyl, methoxy, cyano and/or halogen.

2. A compound of claim 1 of the formula

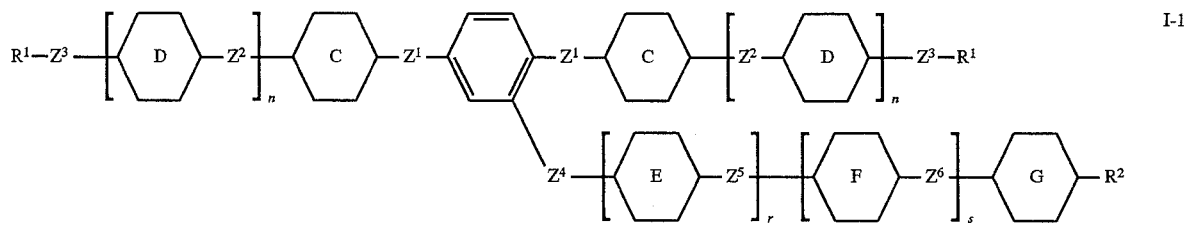

wherein
  rings C and D are independently pyridine-2,5-diyl, pyrimidine-2,5-diyl, trans-1,4-cyclohexylene, trans-1,3-dioxane-2,5-diyl or 1,4-phenylene, which is optionally substituted with halogen, methyl and/or cyano;
  rings E and F are independently pyridine-2,5-diyl, pyrimidine-2,5-diyl, trans-1,4-cyclohexylene, trans-1,3-dioxane-2,5-diyl or 1,4-phenylene, which is optionally substituted with halogen, methyl and/or cyano;
  ring G is 1,4-phenylene, which is unsubstituted or mono- or disubstituted with halogen, methyl, dimethylamino, amino, nitro and/or cyano;
  $Z^1$ is a single bond, —$CH_2CH_2$—, —$CH_2O$—, —COO—, —OOC—, —$(CH_2)_4$— or —$(CH_2)_3O$—;
  $Z^2$, $Z^5$, $Z^6$ each are a single bond, —$CH_2CH_2$—, —$CH_2O$—, —$OCH_2$—, —COO—, —OOC—, —$(CH_2)_4$—, —$O(CH_2)_3$— or —$(CH_2)_3O$—;
  $Z^3$ is —$(CH_2)_m$—, —$(CH_2)_mO$—,
  $Z^4$ is a single bond, —$(CH_2)_p$—, —$(CH_2)_pO$—, —$O(CH_2)_p$—, —$(CH_2)_pCOO$—, —$OOC(CH_2)_p$—, —$(CH_2)_pOOC$—, —$COO(CH_2)$—, —$OOC(CH_2)_pOOC$—, —$O(CH_2)_pOOC$— or —$COO(CH_2)_pO$—; is 0 or 1;
  m,p each are a whole number from 1 to 16; and
  r,s each are 0 or 1; and
  $R^1$ is a cross-linkable group such as acrylate, methacrylate, 2-chloroacrylate, 2-phenylacrylate, acryloylphenylene, acrylamide, methacrylamide, 2-phenylacrylamide, epoxy, itaconic acid ester, vinyl ether, vinyl ester, styrene derivative, maleic acid derivative or fumaric acid derivative or a cinnamic acid derivative, which is optionally substituted with methyl, methoxy, cyano and/or halogen; and
  $R^2$ is an optically active group such as (S)- or (R)-2-butyloxy, (S)- or (R)-2-pentyloxy, (S)- or (R)-2-hexyloxy, (S)- or (R)-2-heptyloxy, (S)- or (R)-2-octyloxy or alkyl, alkoxy or alkanoyloxy with 4 to 8 carbon atoms, which is substituted with methyl, methoxy, cyano and/or halogen.

3. A compound of claim 2 of the formula

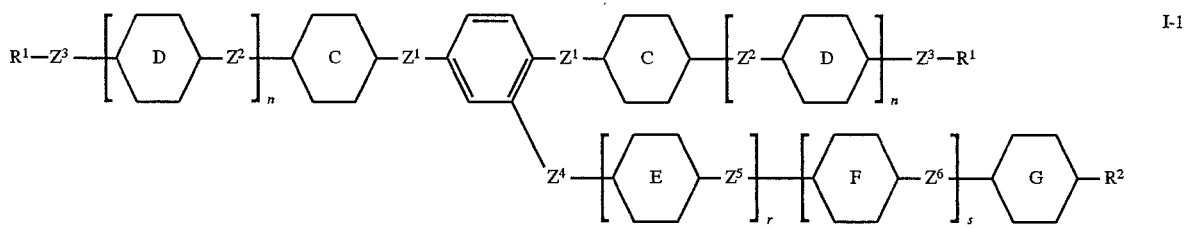

wherein
  rings C and D are independently 1,4-phenylene, 2-fluoro-1,4-phenylene, 3-fluoro-1,4-phenylene, pyridine-2,5-diyl, or pyrimidine-2,5-diyl;
  rings E and F are independently 1,4-phenylene;
  ring G is 2-amino-5-nitro-1,4-phenylene or 5-amino-2-nitro-1,4-phenylene;
  $Z^1$ is —$CH_2O$—, —COO—, —OOC—;
  $Z_2$ is a single bond, —$CH_2CH_2$—, —$CH_2O$—, —$OCH_2$—, —COO—, or —OOC—;
  $Z^5$, $Z^6$ are independently a single bond, —$CH_2CH_2$—, —$CH_2O$—, —$OCH_2$—, —COO—, or —OOC—, —$(CH_2)_4$—, —$O(CH_2)_3$— or —$(CH_2)_3O$—;
  $Z^3$ is —$(CH_2)_m$—, —$(CH_2)_mO$—, —$(CH_2)_mCOO$— or —$(CH_2)_mOOC$—;
  $Z^4$ is a single bond, —$(CH_2)_p$—, —$(CH_2)_pO$—, —$O(CH_2)_p$—, —$(CH_2)_pCOO$—, —$OOC(CH_2)_p$—, —$(CH_2)_pOOC$—, —$COO(CH_2)_p$—, —$OOC(CH_2)_pOOC$—, —$O(CH_2)_pOOC$— or —$COO(CH_2)_pO$—;
  n is 0 or 1;
  m,p each are a whole number from 1 to 16;
  r,s each are 0 or 1;
  $R^1$ is a cross-linkable group such as acrylate, methacrylate, 2-chloroacrylate, 2-phenylacrylate, acryloylphenylene, acrylamide, methacrylamide, 2-phenylacrylamide, epoxy, vinyl ether, vinyl ester, styrene derivative, maleic acid derivative or fumaric acid derivative; and
  $R^2$ is an optically active group such as (S)- or (R)-2-butyloxy, (S)- or (R)-2-pentyloxy, (S)- or (R)-2-hexyloxy, (S)- or (R)-2-heptyloxy, (S)- or (R)-2-octyloxy.

4. A compound of claim 2 wherein rings C and D are independently 1,4-phenylene, 2-fluoro-1,4-phenylene or 3-fluoro-1,4-phenylene.

5. A compound of claim 2 wherein $R^1$ is acrylate, methacrylate, vinyloxy, or epoxy.

6. A compound of claim 1, wherein residues $A^1$ and $A^2$ are the same and have the formula

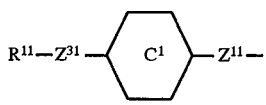
II-a wherein $R^{11}$ is acrylate, methacrylate or epoxy;

$Z^{31}$ is —$(CH_2)_t$—, —$(CH_2)_tO$—, —$(CH_2)_tCOO$— or —$(CH_2)_tOOC$—;

t is a whole number from 4 to 12;

ring $C^1$ is 1,4-phenylene, 2-fluoro-1,4-phenylene or, 3-fluoro-1,4-phenylene; and $Z^{11}$ is —$CH_2O$—, —COO— or —OOC—.

7. A compound of claim 1, wherein residue $A^3$ has the formula

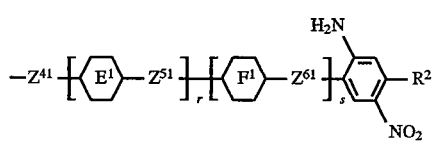
III-a wherein $R^2$ is (S)- or (R)-2-butyloxy, (S)- or (R)-2-pentyloxy, (S)- or (R)-2-hexyloxy, (S)- or (R)-2-heptyloxy or (S)- or (R)-2-octyloxy;

r,s each are 0 or 1;

$Z^{41}$ is —$CH_2CH_2CH_2$—, —$OCH_2CH_2$—, —$CH_2CH_2O$—, —$COOCH_2$— or —$CH_2OOC$—;

$Z^{51}$, $Z^{61}$ each are a single bond, —$CH_2CH_2$—, —$CH_2O$—, —COO—, —OOC, —$(CH_2)_4$— or —$(CH_2)_3O$—; and rings $E^1$ and $F^1$ are 1,4-phenylene.

8. A compound of the formula

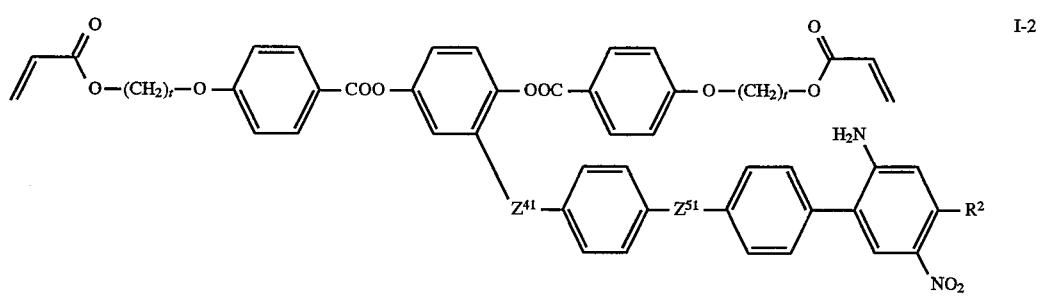
I-2 wherein t is a whole number from 4 to 12;

$R^2$ is (S)- or (R)-2-butyloxy, (S)- or (R)-2-pentyloxy, (S)- or (R)-2-hexyloxy, (S)- or (R)-2-heptyloxy or (S)- or (R)-2-octyloxy;

$Z^{41}$ is —$COOCH_2$—; and $Z^{51}$ is a single bond, —COO— or —OOC—.

9. A compound of claim 7 which is (4-[4-(2-amino-5-nitro-4-[(S)-2-octyloxy]phenyl)benzoyloxy]phenyl)-methyl 2,5-bis(4-[6-acryloyloxyhexyloxy]phenylcarboxy)benzoate.

10. A compound of claim 7 which is (4-[4-(2-amino-5-nitro-4-[(S)-2-octyloxy]phenyl)benzoyloxy]phenyl)-methyl 2,5-bis(4-[11-acryloyloxyundecyloxy]phenylcarboxy) benzoate.

11. A compound of claim 3 which is 4-[4-(2-amino-5-nitro-4- [(S)-2-octyloxy]phenyl)benzoyloxy]butyl 2,5-bis (4-[11-acryloyloxyundecyloxy]phenylcarboxy)benzoate.

12. A composition which comprises at least one compound of claim 1 and at least one compound from the group of compounds of the formulae

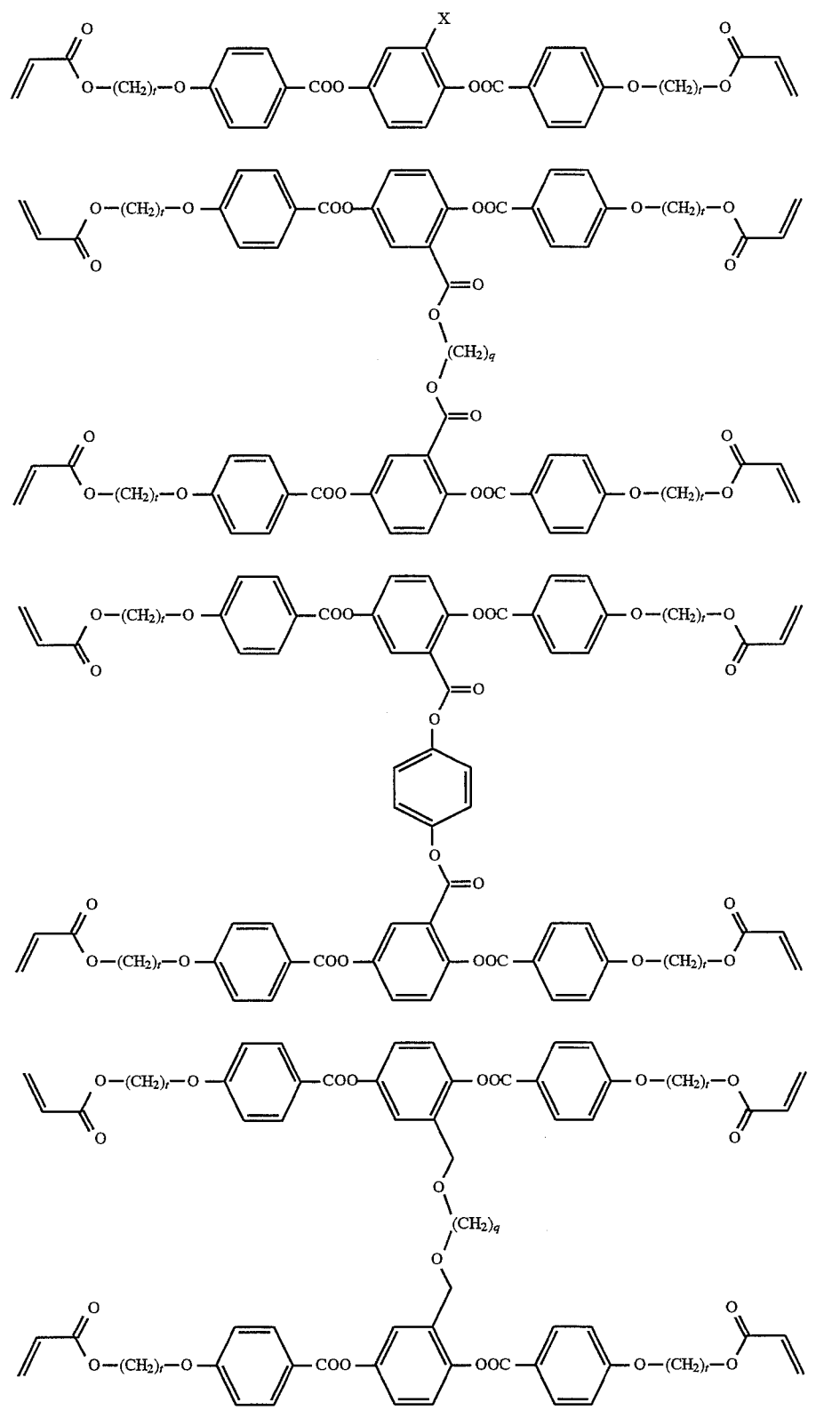

-continued

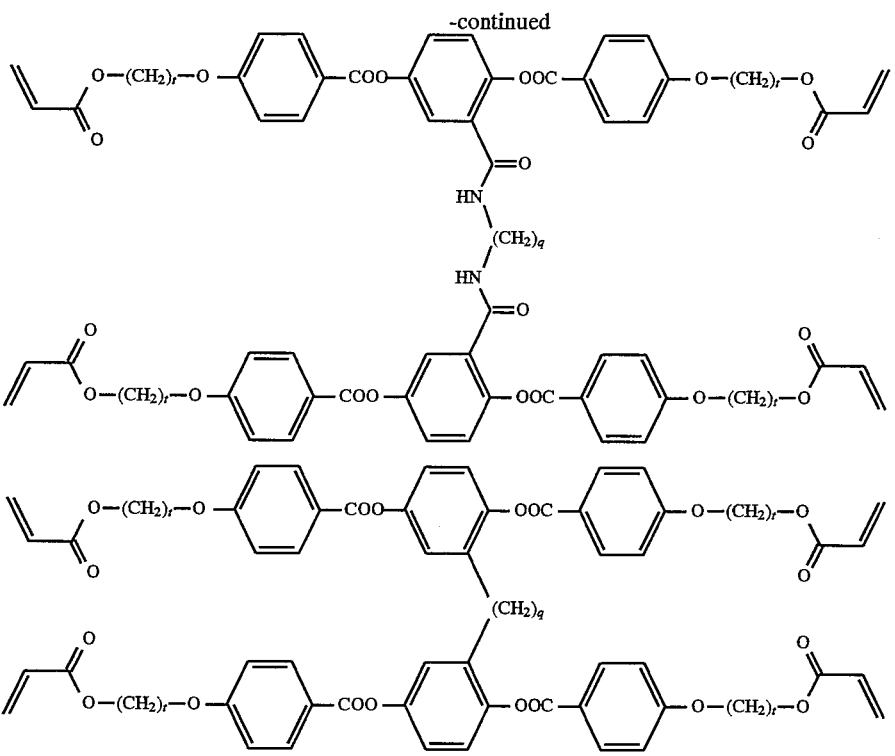

IX

X wherein t signifies a whole number from 4 to 12 and q signifies a whole number from 2 to 12.

13. A composition which comprises a compound of claim 1 and a compound of formula

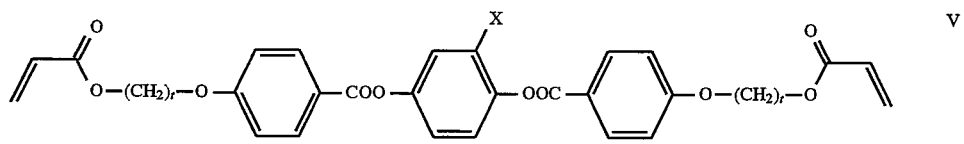

V wherein t signifies a whole number from 4 to 12 and q signifies a whole number from 2 to 12.

14. A composition which comprises a compound of claim 1 and a compound of formula

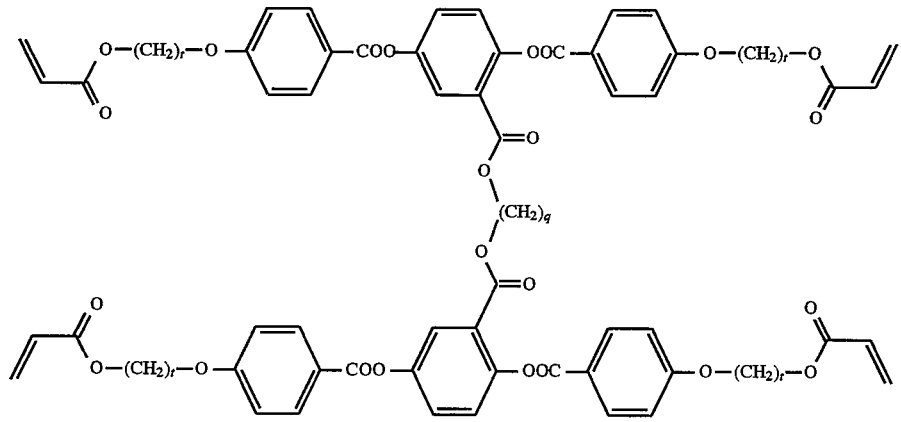

VI wherein t signifies a whole number from 4 to 12 and q signifies a whole number from 2 to 12.

15. A composition which comprises a compound of claim 1 and a compound of formula

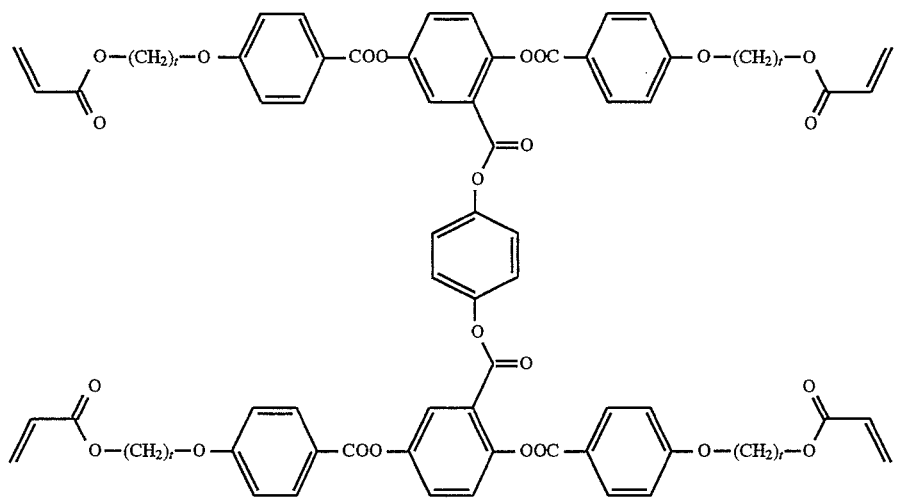
VII wherein t signifies a whole number from 4 to 12 and q signifies a whole number from 2 to 12.

16. A composition which comprises a compound of claim 1 and a compound of formula

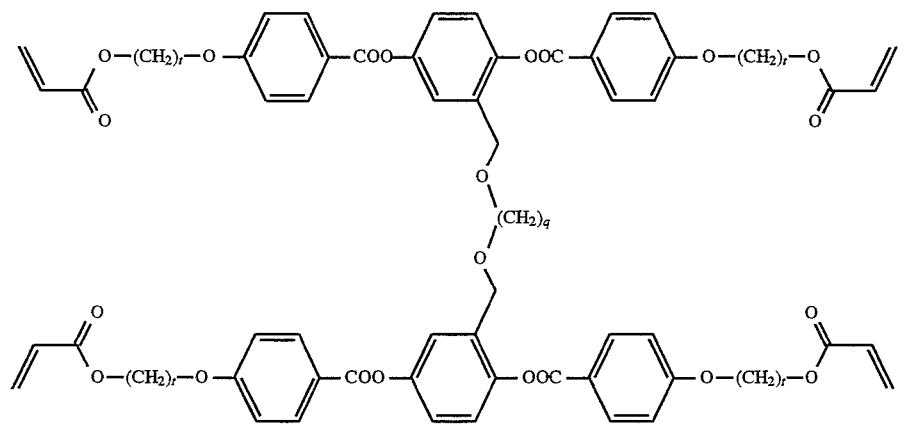
VIII wherein t signifies a whole number from 4 to 12 and q signifies a whole number from 2 to 12.

17. A composition which comprises a compound of claim 1 and a compound of formula wherein t signifies a whole number from 4 to 12 and q signifies a whole number from 2 to 12.

18. A composition which comprises a compound of claim 1 and a compound of formula

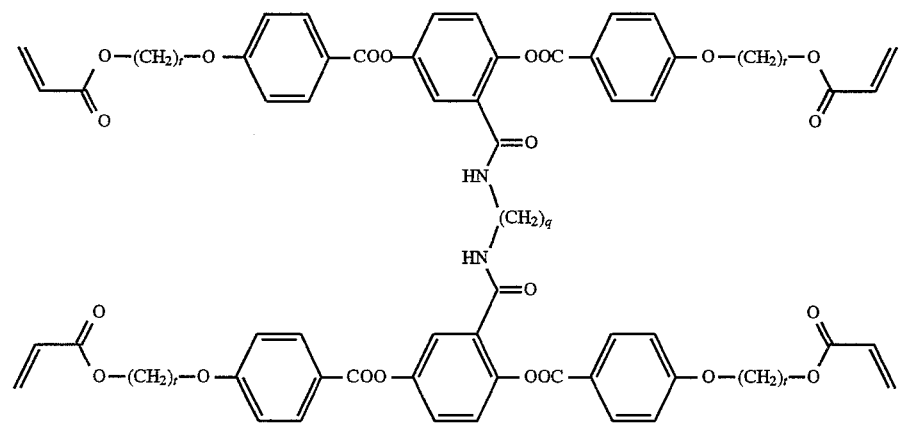
IX

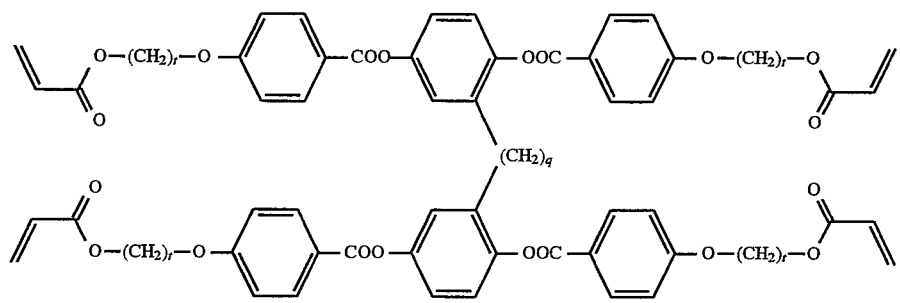
wherein t signifies a whole number from 4 to 12 and q signifies a whole number from 2 to 12.